United States Patent
Grisoni et al.

(10) Patent No.: US 7,506,459 B2
(45) Date of Patent: *Mar. 24, 2009

(54) BALL OF FOOT SHOE INSERTS

(75) Inventors: Bernard F. Grisoni, Cordova, TN (US); Richard T. Avent, Memphis, TN (US); Laura J. Crane, Williston, TN (US)

(73) Assignee: Schering-Plough Healthcare Products, Inc., Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/193,158

(22) Filed: Jul. 29, 2005

(65) Prior Publication Data

US 2006/0026868 A1 Feb. 9, 2006

Related U.S. Application Data

(63) Continuation-in-part of application No. 10/643,172, filed on Aug. 18, 2003, now Pat. No. 7,159,342.

(51) Int. Cl.
*A43B 19/00* (2006.01)
*A61F 5/14* (2006.01)
(52) U.S. Cl. ............................................. 36/71; 36/180
(58) Field of Classification Search .................... 36/71, 36/180, 173–175, 145, 178, 93, 95
See application file for complete search history.

(56) References Cited

U.S. PATENT DOCUMENTS

| | | | | | |
|---|---|---|---|---|---|
| 532,429 | A | * | 1/1895 | Rogers | 36/28 |
| 1,636,044 | A | * | 7/1927 | Connelly | 36/145 |
| 1,867,431 | A | * | 7/1932 | Wood | 36/145 |
| 2,161,565 | A | * | 6/1939 | Freda | 36/180 |
| 2,268,777 | A | * | 1/1942 | Scholl | 128/894 |
| D143,642 | S | * | 1/1946 | Bouthillette | 36/180 |
| 2,475,417 | A | * | 7/1949 | Wysowski | 36/145 |
| 2,580,094 | A | * | 12/1951 | Higgs | 36/145 |
| 2,613,456 | A | * | 10/1952 | Amico | 36/180 |
| 2,660,814 | A | * | 12/1953 | Ritchey | 36/178 |
| 2,917,846 | A | * | 12/1959 | Scholl | 36/145 |
| 3,543,765 | A | * | 12/1970 | Alzner | 36/147 |
| 4,534,121 | A | * | 8/1985 | Autry | 36/35 R |
| 4,739,765 | A | * | 4/1988 | Sydor et al. | 36/174 |
| 5,611,153 | A | * | 3/1997 | Fisher et al. | 36/43 |
| D461,300 | S | * | 8/2002 | Hall | |
| D462,510 | S | * | 9/2002 | Goodrich et al. | |
| D475,184 | S | * | 6/2003 | Polifroni | D2/961 |
| 6,598,321 | B2 | * | 7/2003 | Crane et al. | 36/43 |

(Continued)

*Primary Examiner*—Ted Kavanaugh
(74) *Attorney, Agent, or Firm*—Matthew J. Golden

(57) ABSTRACT

A removable ball of the foot insert for placement into footwear at a position in correspondence with a forefoot portion of the footwear includes a substantially planar member made from a viscoelastic gel, the planar member including a lower surface and an upper surface, and a plurality of spring walls formed from a viscoelastic gel and extending from the lower surface of the planar member at a predetermined area corresponding to a ball of the foot when the insert is inserted into the footwear, for separating bones of second and third metatarsals of the foot, the spring walls having heights that generally decrease outwardly from a center of the predetermined area, and the viscoelastic gel of the planar member having a hardness greater than a hardness of the viscoelastic gel of the spring walls.

10 Claims, 8 Drawing Sheets

U.S. PATENT DOCUMENTS

| | | | |
|---|---|---|---|
| 6,681,501 B1 * | 1/2004 | Polifroni | 36/3 B |
| 7,159,342 B2 * | 1/2007 | Grisoni et al. | 36/180 |
| 2001/0045028 A1 * | 11/2001 | Crane et al. | 36/44 |

* cited by examiner

FIGURE 13
13A
13B

BALL OF FOOT SHOE INSERTS

This application claims priority as a continuation-in-part to U.S. application Ser. No. 10/643,172, filed Aug. 18, 2003. The entire contents of that application are hereby incorporated by reference into the following specification.

INTRODUCTION TO THE INVENTION

The present invention relates generally to shoe inserts, and more particularly, to improved ball of foot shoe inserts that provide cushioning at the ball of the foot, as well as maintaining the insert in position in the shoe.

Ball of foot shoe inserts have generally been formed by a pad of cushioning material of a uniform thickness, such as foam or sponge rubber, that has a general shape conforming to the interior of the shoe at the forefoot. Wearers who desire additional shoe comfort or who suffer from foot trouble, for example, pain at the ball of the foot, place the cushioned insert into the shoe to provide added cushioning and support.

One problem with such known inserts is that, since they do not occupy the entire area of the shoe, they tend to move from a desired position so that the cushioned area thereof is not optimally positioned.

Further, pain at the ball of the foot generally occurs between the second and third metatarsal. This is because the bone structures thereof come together and cause the pain. The uniform thickness of cushioning material of the known ball of foot shoe inserts tends to cushion this area and relieve some pain. However, these ball of foot shoe inserts do not solve the underlying problem of the pain, namely, the bone structures of the second and third metatarsals coming together.

It is also known to provide gel insoles for shoes. Because of the viscous nature of the gel, the gel insoles provide shock absorption and consequently protection to the foot. One reason that gel insoles are popular is that they can be made sufficiently thin to fit in shoes. In order to provide comfort, a soft, absorbent top cloth is adhered to the upper surface of the gel insoles.

However, the shock absorbing quality of the gel insoles has a deleterious effect. Specifically, because of the dampening affect of the gel, walking can require more energy, causing the muscles to get tired more easily. For this reason, gel insoles have been proposed, as disclosed in U.S. patent Publication No. 2003/0024134 to the same assignee herein, published Feb. 6, 2003, and different gel insoles have also have been sold by the assignee of the present application under the trademark DR. SCHOLL'S Massaging Gel Insoles and which are the subject of U.S. Pat. No. 6,598,321, to overcome this problem.

Specifically, these latter massaging gel insoles are formed of a lower gel layer and a top cover secured to the upper surface of lower gel layer. Thin and spaced apart elastic and resilient spring walls in sinusoidal shaped wave patterns are formed in a repeating order within a first recess formed in the toe portion and a second recess formed in the heel portion. The recesses occupy a substantial central area of the toe portion and heel portion, respectively, with the thin spring walls extending substantially transversely from one side to the other side of the recesses and integrally formed as a unitary, one-piece structure with the peripheral side walls and top walls of the recesses. The height of the spring walls is the same as the height of the recesses so that lower edges of thin spring walls are substantially coplanar with the lower surface of the insole.

The reason for providing the thin, spaced apart spring walls in the recesses of the toe portion and heel portion, is that these are the areas where the major forces are exerted on the insole during heel impact and during push off. With this arrangement, the gel material of the lower gel layer is more viscous than elastic, which provides a high degree of energy absorption by the gel. On the other hand, the thin flexible and resilient spring walls are more elastic than viscous, which provides a quicker acting spring than the gel of the remainder of lower gel layer, but with less dampening energy absorption. Thus, when a force is applied to thin spring walls, the response is more like a spring than as a damper, while the base gel of the remainder of lower gel layer has an opposite response, that is, acting more like a damper than a spring. This combination of the more viscous base gel and the more elastic thin spring walls gives the insole a unique feature of a fast reaction on first heel impact and a slower higher damped energy absorption as the heel recedes into the viscous base of the insole. When the heel recedes from the insole, the reverse action occurs, that is, thin spring walls return some of the spring action to the heel. When the foot moves to push off, the action of the insole is the same. In other words, this combination of the more viscous base gel and the more elastic thin spring walls gives the insole a unique feature of a fast reaction on first forefoot impact and a slower higher damped energy absorption as the forefoot recedes into the viscous base of insole. When the forefoot recedes from insole, the reverse action occurs, that is, the thin spring walls return some of the spring action to the forefoot, giving the foot a softer impact and a springy push off.

However, the gel material of the sinusoidal shaped, resilient spring walls and the remainder of the insole are formed from the same hardness material. The difference in viscosity and elasticity between the spring walls and the remainder of the insole is due to the construction alone, and not by the use of different materials. There is no reason to provide the gel material of the sinusoidal shaped, resilient spring walls and the remainder of the insole from different hardness materials, since the insoles occupy the entire area of the shoe, and there is no problem with slipping of the insoles, as occurs with ball of the foot insoles which do not occupy the entire area of the shoe.

Further, with these known insoles, the resilient spring walls are all made of a uniform height and extend coplanar with the lower surface of the insole. Therefore, these known insoles do not raise the ball of the foot, and therefore, do not function to solve the underlying problem of pain caused by the bone structures of the second and third metatarsals coming together.

SUMMARY OF THE INVENTION

Accordingly, it is a feature of the present invention to provide a ball of the foot insert that overcomes the problems with the aforementioned prior art. It is another feature of the present invention to provide a ball of the foot insert that functions to raise the ball of the foot to separate the bones of the second and third metatarsals.

It is still another feature of the present invention to provide a ball of the foot insert that provides different heights of the sinusoidal shaped, resilient spring walls to better separate the bones of the second and third metatarsals.

It is yet another feature of the present invention to provide a ball of the foot insert that provides a gel material of a greater hardness in areas surrounding the resilient spring walls to better retain the insert in a desired position in the shoe.

It is a further feature of the present invention to provide a ball of the foot insert that provides a shock dampening affect of the gel material, while also providing a spring action push-off for walking.

It is a still further feature of the present invention to provide a ball of the foot insert that provides comfort to a person's feet, without causing the muscles to tire easily.

It is a yet further feature of the present invention to provide a ball of the foot insert having a low friction fabric on the upper surface which reduces forces from the foot that would tend to move the insert in the shoe.

It is an additional feature of this invention to provide a ball of foot insert comprising a tackified lower surface which provides additional means for maintaining the insert in the proper location in the shoe.

In accordance with an aspect of the present invention, a removable ball of the foot insert for placement into footwear at a position in correspondence with a forefoot portion of the footwear includes a substantially planar member including a lower surface and an upper surface, and a raised area at a predetermined location corresponding to a ball of the foot when the insert is placed into the footwear for separating bones of second and third metatarsals of the foot.

The raised area has a height that generally decreases outwardly from a center of the raised area, and preferably has a generally convex shape. In addition, a low friction cover layer is secured to the upper surface of the planar member.

In accordance with another aspect of the present invention, a removable ball of the foot insert for placement into footwear at a position in correspondence with a forefoot portion of the footwear includes a substantially planar member made from a viscoelastic gel, the planar member including a lower surface and an upper surface, and a plurality of spaced apart spring walls formed from a viscoelastic gel and extending from the lower surface of the planar member at a predetermined area corresponding to a ball of the foot when the insert is inserted into the footwear, for separating bones of second and third metatarsals of the foot, the spring walls having heights that generally decrease outwardly from a center of the predetermined area.

In one embodiment of the invention, the viscoelastic gel of the planar member has a hardness greater than a hardness of the viscoelastic gel of the spring walls. For example, the viscoelastic gel of the planar member has a Shore OO hardness of about 65 to about 75, and the viscoelastic gel of the spring walls a Shore OO hardness of about 40 to about 50.

In another embodiment of the invention, the composition of the planar member and the spring walls have the same hardness.

In one embodiment, each spring wall extends in a generally lengthwise direction of the insert. In an equally preferred embodiment, each spring wall extends generally in a curve with the apex of the curve located generally near the center of the insert. In this embodiment, the spring walls can be divided into a plurality of curved spring walls, each segment comprising a plurality of spring walls substantially parallel to one another, and the apex of the curvature of the segment of spring walls pointing substantially towards the apex of the curvature of another segment. Each spring wall has a height that decreases from a center thereof toward opposite ends thereof, and spring walls on opposite sides of a center one of the spring walls decrease in height transversely to an extending direction of the center one of the spring walls.

Preferably, the insert has a substantially teardrop shape, and includes a low friction cover layer secured to the upper surface of the planar member.

Preferably, each of the spring walls is formed in a generally sinusoidal wave shape, and the plurality of spring walls are formed in substantially parallel, spaced apart relation, with a spacing between adjacent ones of the spring walls being greater than the width of the spring walls.

In accordance with still another aspect of the present invention, a removable ball of the foot insert for placement into footwear at a position in correspondence with a forefoot portion of the footwear, includes a substantially planar member made from a viscoelastic gel, the planar member including a lower surface and an upper surface, a raised area formed from a viscoelastic gel and extending from one of the lower surface and upper surface of the planar member at a predetermined area corresponding to a ball of the foot when the insert is inserted into the footwear, for separating bones of second and third metatarsals of the foot, and the viscoelastic gel of the planar member having a hardness greater than a hardness of the viscoelastic gel of raised area.

The above and other features of the invention will become readily apparent from the following detailed description thereof, which is to be read in connection with the accompanying drawings.

BRIEF DESCRIPTION OF THE DRAWINGS

FIGS. 13A and B are the cross section views of the right and left ball of foot insert referred to in FIGS. 12A and B, respectively.

DETAILED DESCRIPTION

Figure 1:
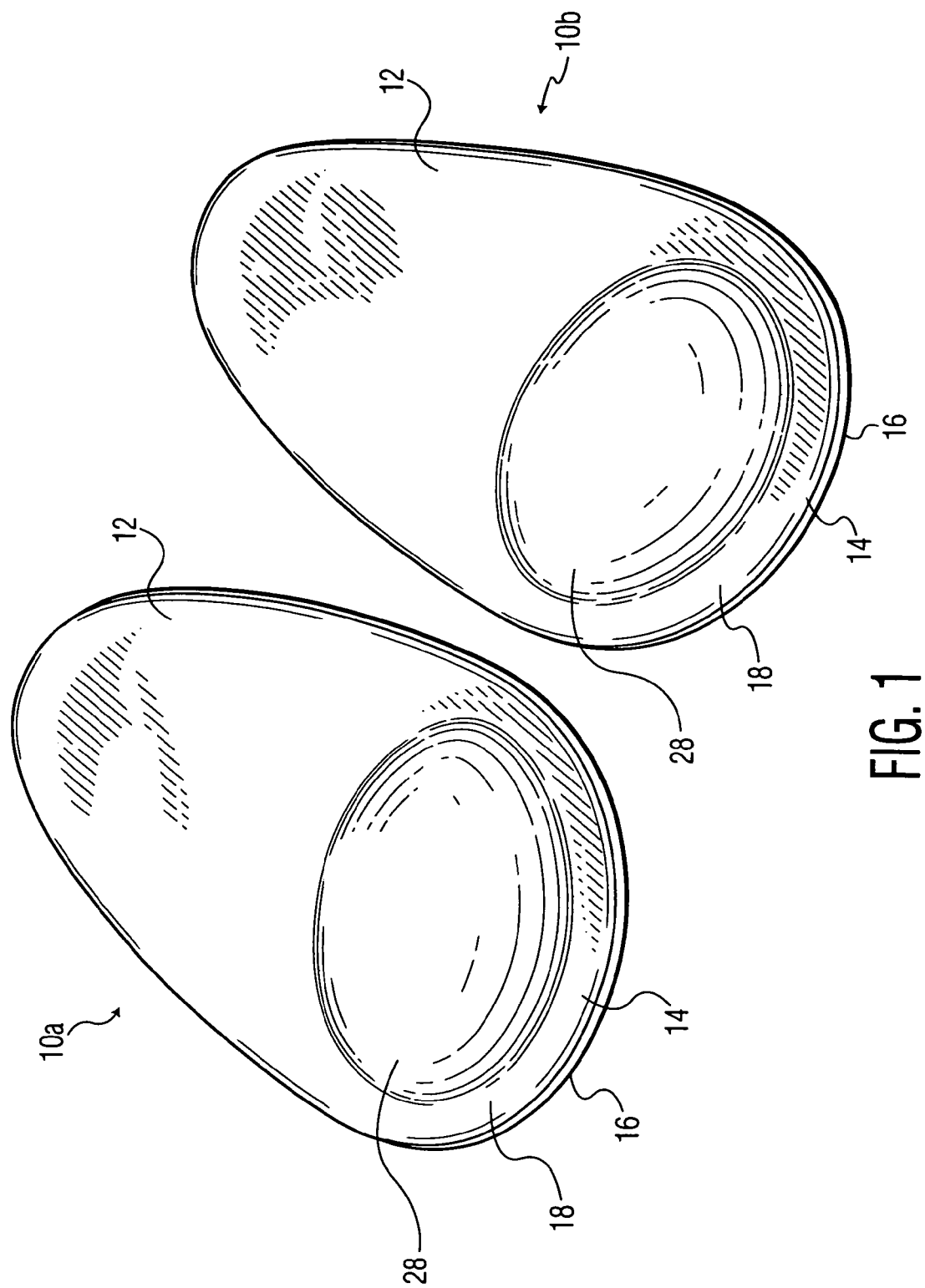
FIG. 1 is a top perspective view of ball of foot inserts according to the present invention for the left and right feet.
Figure 2:
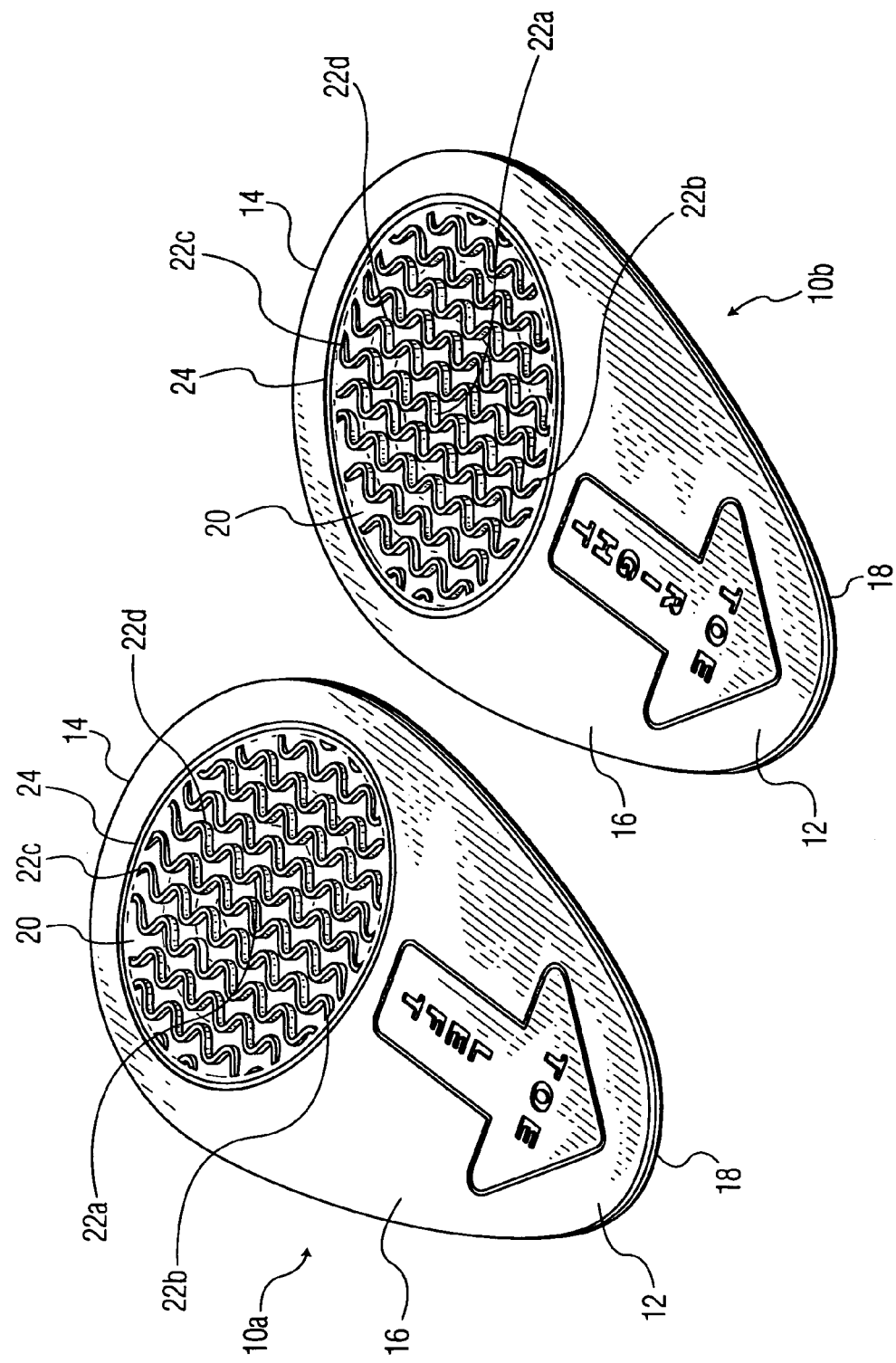
FIG. 2 is a bottom perspective view of the ball of foot inserts of FIG. 1.
Figure 3:
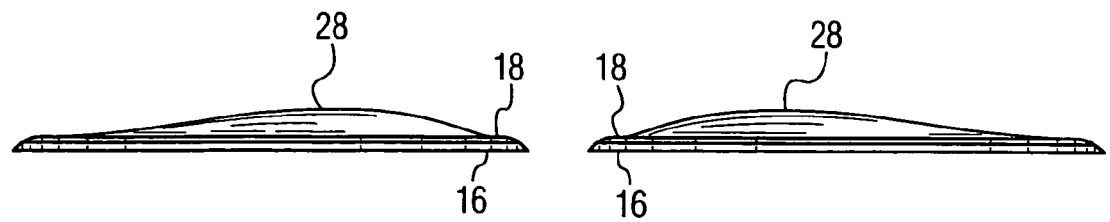
FIG. 3 is a front elevational view of the ball of foot inserts of FIG. 1.
Figure 4:
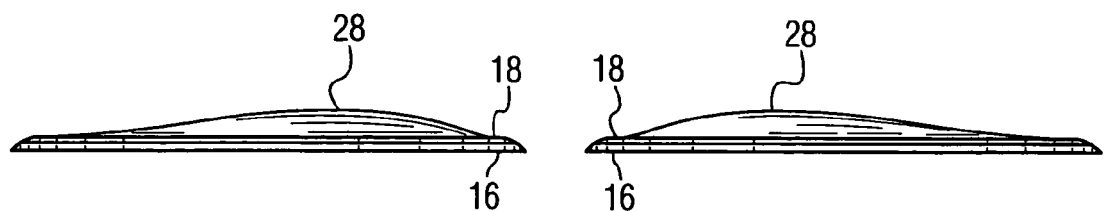
FIG. 4 is a rear elevational view of the ball of foot inserts of FIG. 1.
Figure 5:
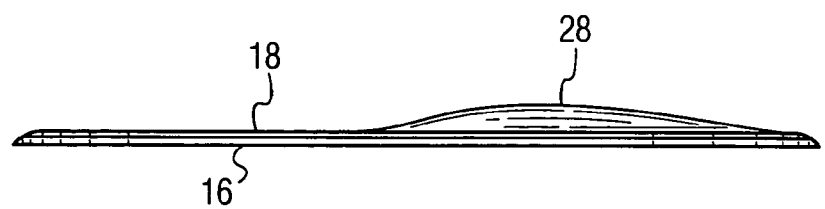
FIG. 5 is a right elevational view of either ball of foot insert of FIG. 1.
Figure 6:
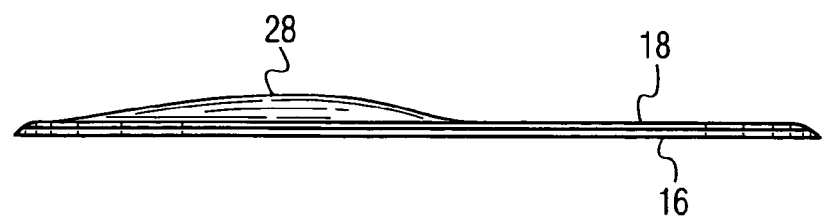
FIG. 6 is a left elevational view of either ball of foot insert of FIG. 1.
Figure 7:
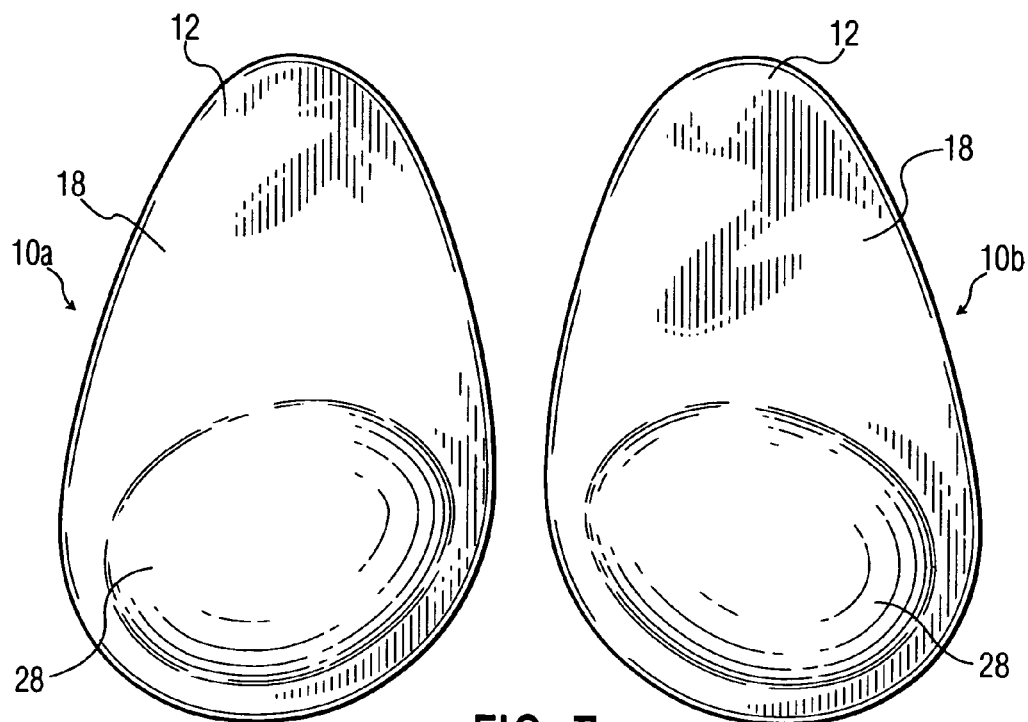
FIG. 7 is a top plan view of the ball of foot inserts of FIG. 1.
Figure 8:
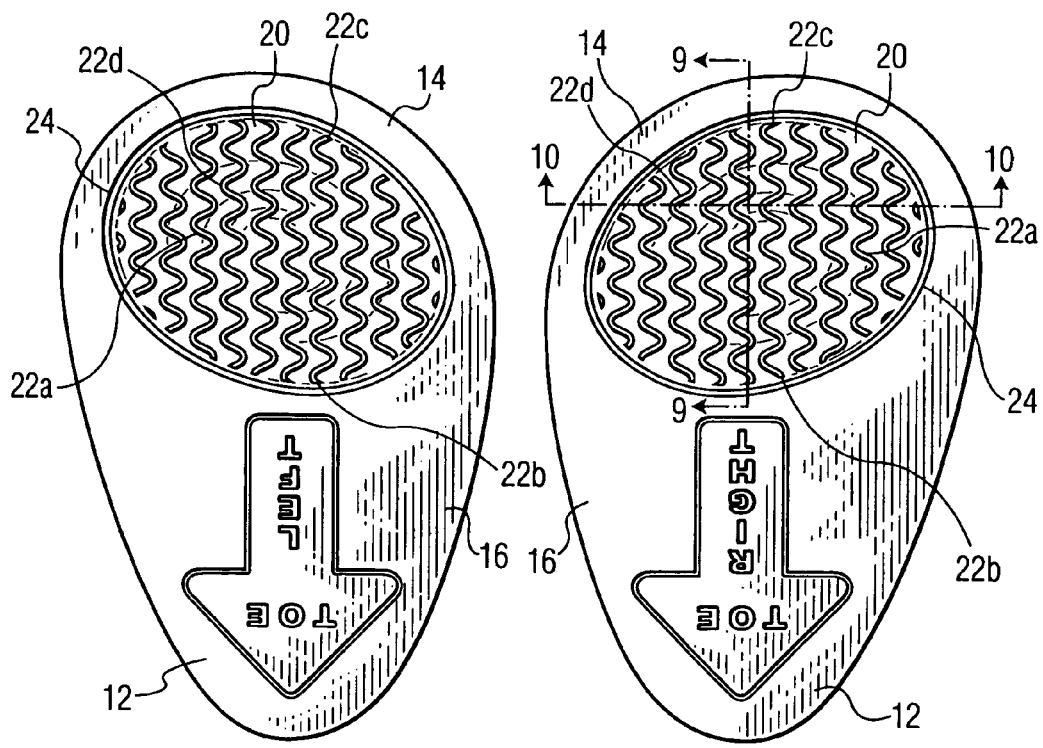
FIG. 8 is a bottom plan view of the ball of foot inserts of FIG. 1.
Figure 9:
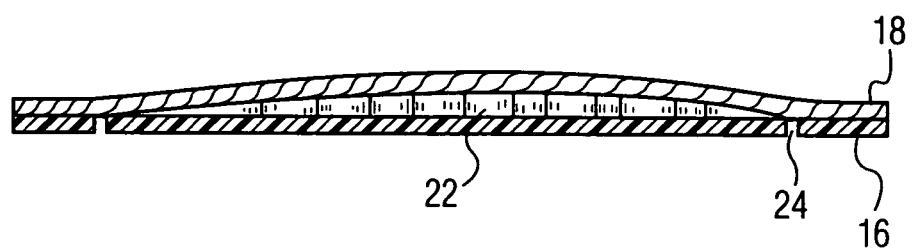
FIG. 9 is a cross-sectional view of the right ball of foot insert of FIG. 8, taken along line 9-9 thereof.
Figure 10:
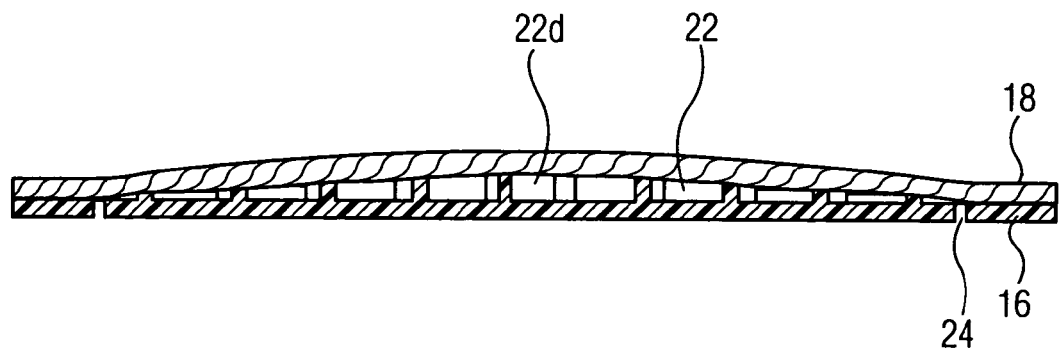
FIG. 10 is a cross-sectional view of the right ball of foot insert of FIG. 8, taken along line 10-10 thereof.
Figure 11:
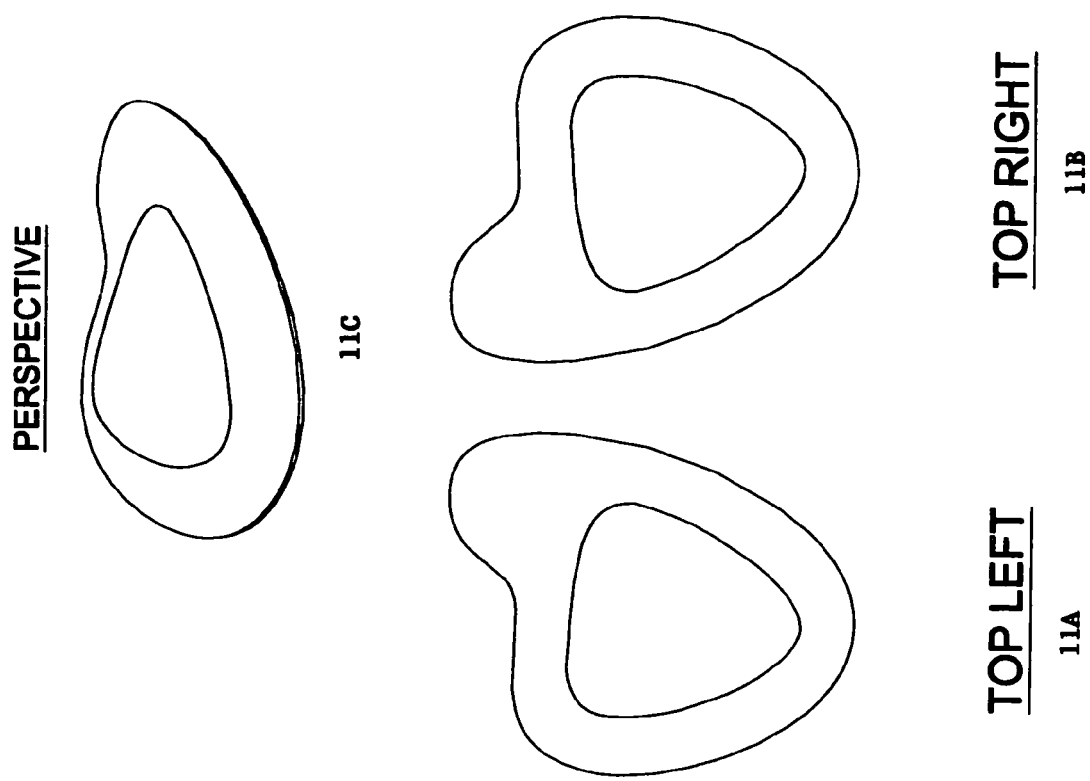
FIGS. 11A, B, and C are top perspective views of an additional embodiment of ball of foot inserts according to the present invention for the left and right feet.

As used herein, the terms insert and insole are used synonymously.

Referring to the drawings in detail, left and right ball of foot inserts 10a and 10b according to a first embodiment of the present invention are adapted to be placed into an article of footwear for supporting the forefeet of a person, as is well known. Ball of foot inserts 10a and 10b are particularly adapted to be placed into a woman's pointed toe high heeled shoes since there is excessive force placed on the ball of the feet, although the present invention is not limited thereto. Accordingly, inserts 10a and 10b each preferably have the shape of the front portion of a woman's pointed high-heeled shoe. Inserts 10a and 10b therefore each include a curved toe portion 12 which increases in width toward the rear portion 14 thereof which terminates at its proximal portion immediately in front of the arch area of the shoes, such that inserts 10a and 10b each have a generally teardrop shape.

Each insert 10a and 10b is formed of a lower gel layer 16 and a top cover 18 secured to the upper surface of lower gel layer 16 by any suitable means, such as adhesive, radio frequency welding, mechanical bonding, etc. Both layers 16 and 18 are preferably formed of a relatively fluid impermeable material.

Lower gel layer 16 is made from a non-foam elastomer such as the class of materials known as viscoelastic polymers or silicone gels, which show high levels of damping when tested by dynamic mechanical analysis performed in the range of −50° C. to 100° C. Because the mechanical properties of the gel are more viscous than elastic, the gel provides a high degree of energy absorption. Gels that can be used according to the present invention are thermoset or thermoplastic elastomers (elastomeric materials), such as materials made from many polymeric families, including but not limited to styrene-olefin-rubber block copolymers, thermoplastic polyurethanes, thermoset polyurethanes, thermoplastic polyolefins, polyamides, polyureas, polyesters and other polymer materials that reversibly soften as a function of temperature. A preferred elastomer is a block copolymer of styrene/ethylene-co-butylene/styrene or styrene/butadiene/styrene, with mineral oil incorporated into the matrix as a plasticizer. Such preferred elastomers are sold by Kraton Polymers of Houston, Tex. U.S.A. using the trademark KRATON.

Figure 12:
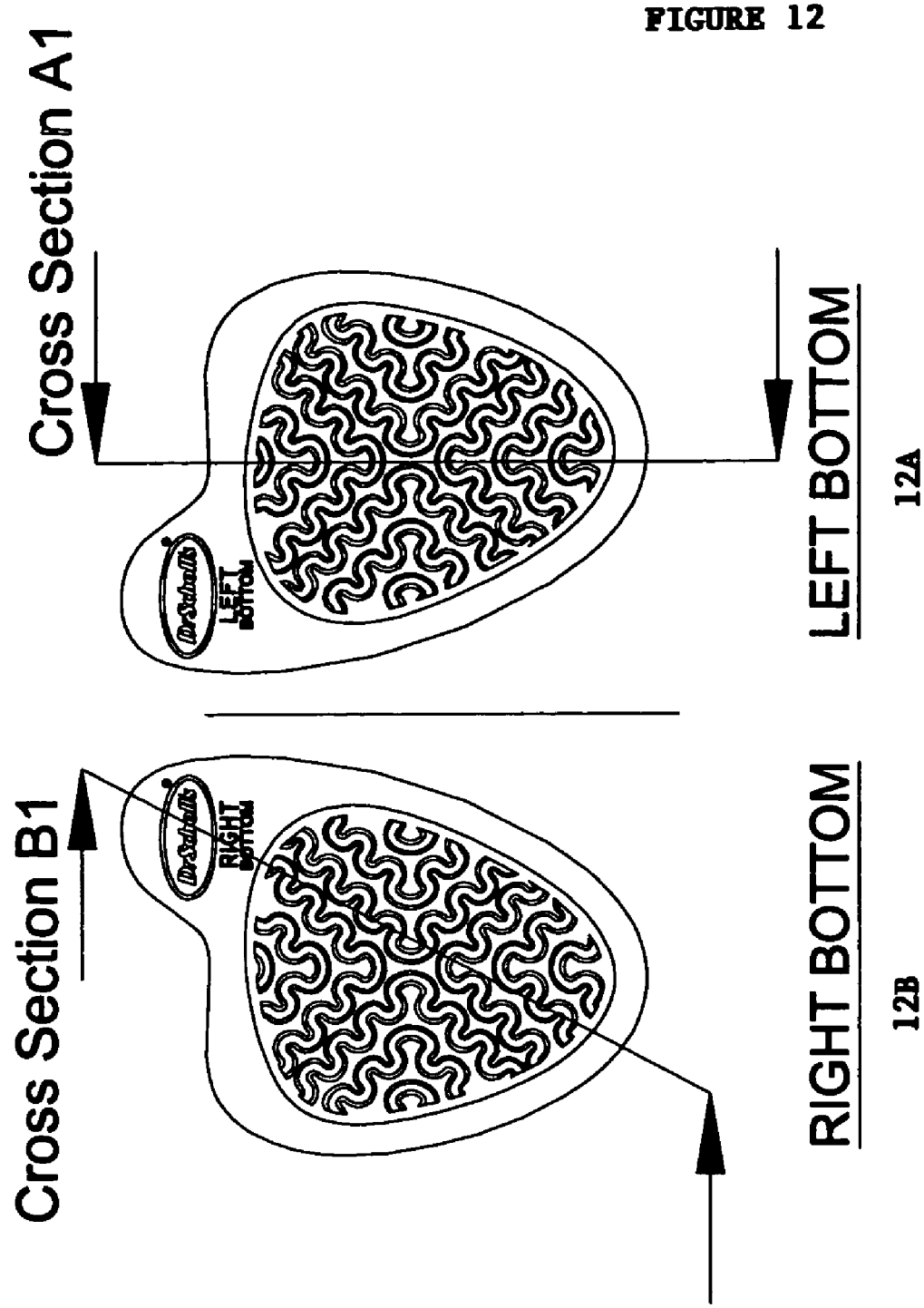
FIGS. 12A and B are the bottom perspective views of the ball of foot inserts of FIG. 11, in addition demonstrating sinusoidal spring walls arranged in generally curved relation with the apex of curvature pointed generally at the center of the insert.

Thin and spaced apart elastic and resilient spring walls 22 are formed in a repeating order and extend downwardly from an upper layer 20 of gel within an area 24 formed in toe portion 12. Area 24 occupies a substantial central area of rear portion 14 at a position corresponding to the ball of the foot, with thin spring walls 22 extending in a substantially lengthwise direction of the insert within area 24 and integrally formed as a unitary, one-piece structure with the upper layer 20 of gel of area 24. It will be appreciated that spring walls 22 are not limited to extending in a lengthwise direction of insert 10, and can extend transversely thereto, or at an angle therebetween. As demonstrated in FIGS. 12A and 12B, the spring walls 22 can be arranged in a generally curved relationship. In one embodiment, a plurality of sections of generally curved spring walls can be arranged such that the apex of the curvature of the spring walls points generally towards the center of the insert, extending radially out therefrom.

In accordance with an important aspect of the present invention, the height of each spring wall 22 decreases from a center point 22a thereof toward the opposite ends 22b and 22c thereof. In like manner, the centermost spring wall 22d is at a maximum height and the spring walls 22 reduce in height transversely from the centermost spring wall 22d. In this manner, the greatest height of spring walls 22 is at the center point 22a of the centermost spring wall 22d. As a result, the lower surfaces of spring walls 22 form a substantially convex or part-spherical shape. When an insert 10a or 10b is placed in a shoe, the lower surfaces of spring walls 22 lie substantially coplanar in the shoe. As a result of the different heights, upper gel layer 20 is bowed upwardly to form a substantially convex or part-spherical shape in use.

Because of the elastic and resilient nature of spring walls 22, a cushion effect is provided for the ball of the foot of the person. Thin flexible and resilient spring walls 22 are elastic and therefore also provide the function of a quick acting spring. When the foot first impacts the forefoot portion, the foot acts to apply a load and the gel material functions to absorb the shock. As the foot moves to push off, and particularly, when the forefoot recedes from insert 10, thin spring walls 22 return some of the spring action to the forefoot, giving the foot a softer impact and a springy push off.

More importantly, however, because of the substantially convex or part-spherical bulge 28 presented to the ball of the person's foot on top cover 18, the ball of the foot is raised up in a manner to separate the bones of the second and third metatarsals in order to remove, or at least alleviate, the source of the pain. Thus, bulge 28 provides an anatomical correction to the bones of the foot to alleviate pain at the ball of the foot.

Thin spring walls 22 preferably have a height of about 2 to about 3 mm and a thickness or width of approximately 1.5 mm, while the height of upper layer 20 is about 1 mm to about 2 mm. Top cover preferably has a height of about 1 mm.

In the above embodiment, thin, spaced-apart spring walls 22 are formed as parallel, spaced, sinusoidal shaped wave patterns. However, the present invention is not so limited, and may take other shapes, such as those disclosed in U.S. Pat. No. 6,598,321 and U.S. patent Publication No. 2003/0024134, the entire disclosures of which are incorporated herein by reference. Examples of other shapes include a columnar shape, that is, formed as a plurality of parallel, spaced, discrete cylindrical columns in each area 24, a plurality of parallel, spaced, discrete columns of triangular sectional configurations in each area 24, a hemispherical shape, that is, formed as a plurality of spaced hemispheric shaped walls in each area 24, substantially conical shaped walls with rounded free ends, a spiral shape, etc.

Further, although twelve transverse rows of thin spring walls 22 are shown with a spacing of approximately 4 mm between adjacent rows, the present invention is not so limited, and this number may vary by changing the amplitude of the sinusoidal wave patterns and/or spacing between the sinusoidal wave patterns. In addition, the pitch of the sinusoidal wave patterns in the transverse direction may also be varied.

In addition, although the present invention is formed from a gel material in order to create the bulge 28 by means of spring walls 22, bulge 28 can be created in other ways. For example, insert 10 can be made from a conventional foam material with an increased thickness in a predetermined area corresponding to the ball of the foot in order to create the bulge, or an additional material can be secured below or above the foam material of the insert in order to create the bulge.

In accordance with another important aspect of the present invention, the gel which forms spring walls 22 is made of a softer elastomer than the gel which forms upper layer 20 and the remainder of insert 10a and 10b surrounding areas 24. Preferably, the gel which forms spring walls 22 has a Shore OO hardness of about 40 to about 50, while the gel which forms upper layer 20 and the remainder of insert 10a and 10b surrounding areas 24 has a Shore OO hardness of about 65 to about 75.

Hardness of a material can be measured by a number of commercially available instruments, including the SHORET™ Durometers sold by Instron Corporation of Canton, Mass. U.S.A. The technique for such measurement is very well known in the art.

The use of the harder gel, which forms upper layer 20 and the remainder of insert 10a and 10b surrounding areas 24, functions to better form a non-slip area with the shoe, that is, to better retain inserts 10a and 10b in position without slipping. In such case, the harder gel provides little or no cushioning effect. On the other hand, the softer gel of spring walls 22 functions to provide the desired cushioning effect and spring effect, as described above. As a result of using gels of two different hardnesses, there is a maximum cushioning effect and maximum holding of inserts 10a and 10b in desired positions within a shoe.

Top cover 18 can be made from any suitable material such as fabric, leather, leatherboard, expanded vinyl foam, flocked vinyl film, coagulated polyurethane, latex foam on scrim, supported polyurethane foam, laminated polyurethane film or in-mold coatings such as polyurethane, styrene-butadiene-rubber, acrylonitrile-butadiene, acrylonitrile terpolymers and copolymers, vinyls, or other acrylics, as integral top covers. Desirable characteristics of top cover 18 include good durability, stability and visual appearance. Also desired is that the material of top cover 18 have good flexibility, as indicated by a low modulus, in order to be easily moldable. The bonding surface of top cover 18 should provide an appropriate texture in order to achieve a suitable mechanical bond to lower gel layer 16.

In accordance with another aspect of the present invention, top cover 18 is made from a low friction fabric, that is, top cover 18 is somewhat slippery so that there is not a large amount of friction between the person's foot and top cover 18 that would otherwise tend to move inserts 10a and 10b out of position. In this manner, the feet can move in the shoes without displacing inserts 10a and 10b. A preferred low friction material that can be used is a synthetic fabric containing stretch fibers sold by E. I. duPont de Nemours and Company of Wilmington, Del. U.S.A. under the trademark LYCRA.

In accordance with a further aspect of the present invention, the lower surface 16 of the insole of the invention can be secured to the footwear by using the tack properties of the gel materials used or by adding a tackifier to the insole. In this regard, it is preferred that the tack of the gel is enhanced by incorporating a tackifier into the gel composition to increase the friction/tack of the gel surface. Suitable tackifiers include a petroleum hydrocarbon resin sold under the designation I-Mark V by Idemitsu Kosan Co., Ltd. of Tokyo, Japan; the rosin sold under the trademark ASYLVALITE® under designation RE 80 for SEBS gels; and phenolsulfonic acid ester sold under the trademark AMESAMOLL® for a polyurethane (PU) gel. The desired tack is preferably between 120 and 250 grams, as determined by a probe tack tester sold under the trademark APOLYKEN®, at one second contact time. Thus, in a preferred embodiment, the tackified lower surface 16 provides an insole with the upper surface 20 of the insole comprising a lower coefficient of friction than the lower surface. The difference in the coefficient of friction between the upper and lower surfaces of the insole can be enhanced by including the tackified lower surface on an insole with a low friction top surface as described above.

Having described specific preferred embodiments of the invention with reference to the accompanying drawings, it will be appreciated that the present invention is not limited to those precise embodiments and that various changes and modifications can be effected therein by one of ordinary skill in the art without departing from the scope or spirit of the invention as defined by the appended claims.

What is claimed is:

1. A removable ball of the foot insert for placement into footwear at a position in correspondence with a forefoot portion of the footwear, comprising:
    a substantially planar member made from a viscoelastic gel, the planar member including a lower surface and an upper surface; and
    a plurality of spaced apart spring walls formed from a viscoelastic gel and extending from the lower surface of the planar member at a predetermined area corresponding to a ball of the foot when the insert is placed into the footwear, for separating bones of second and third metatarsals of the foot, said spring walls having heights that generally decrease outwardly from a center of said predetermined area;
    wherein the viscoelastic gel of the planar member has a hardness greater than a hardness of the viscoelastic gel of the spring walls;
    wherein said viscoelastic gel comprises a tackifier; and
    wherein said insert comprises a low friction cover layer secured to said upper surface.

2. The removable ball of the foot insert according to claim 1, wherein each spring wall extends in a generally lengthwise direction of the insert.

3. The removable ball of the foot insert according to claim 1, wherein each spring wall extends generally along a curve, the apex of which is located generally in the center of the insert.

4. The removable ball of the foot insert according to claim 1, wherein each spring wall has a height that decreases from a center thereof toward opposite ends thereof.

5. The removable ball of the foot insert according to claim 1, wherein spring walls on opposite sides of a center one of the spring walls decrease in height transversely to an extending direction of the center one of the spring walls.

6. The removable ball of the foot insert according to claim 1, wherein the insert has a substantially teardrop shape.

7. The removable ball of the foot insert according to claim 1, wherein each of said spring walls is formed in a generally sinusoidal wave shape.

8. The removable ball of the foot insert according to claim 7, wherein said plurality of spring walls are formed in substantially parallel, spaced-apart relation.

9. The removable ball of foot insert according to claim 8, wherein a spacing between adjacent ones of said spring walls is greater than the width of said spring walls.

10. The removable ball of foot insert according to claim 7 wherein said generally sinusoidal wave shaped spring walls is arranged in generally curved relation wherein the apex of curvature points generally at the center of the insert.

* * * * *